(12) United States Patent
Herrmann et al.

(10) Patent No.: US 6,589,921 B2
(45) Date of Patent: Jul. 8, 2003

(54) CYCLIC COMPOUNDS AND THEIR USE AS PRECURSORS OF FRAGRANT ALCOHOLS

(75) Inventors: Andreas Herrmann, Geneva (CH); Jean-Yves Billard De Saint-Laumer, Beaumont (FR); Otto Gräther, Carouge (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/115,490

(22) Filed: Apr. 2, 2002

(65) Prior Publication Data

US 2002/0169087 A1 Nov. 14, 2002

Related U.S. Application Data

(62) Division of application No. 09/943,192, filed as application No. PCT/IB00/00315 on Mar. 21, 2000.

(30) Foreign Application Priority Data

Mar. 26, 1999 (CH) ............................................. 0579/99

(51) Int. Cl.$^7$ ........................... C11D 3/50; A61K 7/46; C07C 49/76; C07C 47/542
(52) U.S. Cl. ........................ 510/102; 512/21; 568/336; 568/442
(58) Field of Search .................... 510/105, 106, 510/107, 102; 512/21; 568/336, 442

(56) References Cited

U.S. PATENT DOCUMENTS 4,521,331 A * 6/1985 Martel et al. ................ 252/522

FOREIGN PATENT DOCUMENTS

| DE | 197 50 706 A1 | 5/1998 |
|---|---|---|
| GB | 2 319 527 | 5/1998 |
| JP | 61197552 | 9/1996 |
| WO | WO 95/04809 | 2/1995 |
| WO | WO 98/07814 | * 2/1998 |
| WO | WO 98/47478 | * 10/1998 |

OTHER PUBLICATIONS

N. Gautier and R.H.Dodd, Synthetic Communicaitions 1998, 28 (20) 3769–3777, Sep. 1998.*
J. Barry et al., Synthesis 1985, 40–45, Jan. 1985.*
L. Horner and J. Klaus, Liebigs Annalen der Chemie 1979, 1232–1257, Jun. 1979.*
J. A. Wenninger et al., International Cosmetic Ingredient Dictionary and Handbook, 7$^{th}$ ed., 1997, vol. 1, p. 6, Cosmetic, Toiletry and Fragrance Association, Washington, DC, Dec. 1997.*
Beilstein Information Service File: XFire, XP002140854. see BRBs: 4504558, 4251994, 2693192, 2651922, 4812476, 3106865.

L Horner et al., "Moglichkeiten und Grenzen phototochemisch induzierter asymmetrischer Synthesen", Verlag Chemie, GmbH pp. 1232–1257 (1979).
A. Kotali et al, "Synthesis Of o–Ketoaryl–Carboxylic Esters Using Phenyliodoso Diacetate",OPPI Briefs, vol. 28, No. 5 pp. 622–627 (1996).
H. Gordon et al, "Optical Activity and the Polarity of Substituent Groups. Part III. Menthyl Acetophenone–o–carboxylate", Journal of Chem. Science, pp. 553–556.
M. Vivekananda Bhatt et al., "Aspects of Tautomerism, 6$^{1a,b}$ Base–Catalyzed Hydrolysis of Pseudo Esters of γ–keto Acids", J. Org. Chem., vol. 42, No. 16, pp. 2697–2701 (1977).
N. Gautier et al., "The Practical Use of a Glycine Anion Equivalent For The Preparation of 3–Carboxy–1–2–Dihydro–1–Oxoisoquinoline" Synthetic Communications, vol. 28, No. 20, pp. 3769–3977 (1998).
Bram et al, "Solid–Liquid Phase Transfer Catlysis without Addied Solvern. A Simple, Efficient, and Inexpensive Synthesis of Aromatic Carboxylic Esters By Alkylation of Patasium Carboxylates" Communications, pp. 40–45 (1985).

* cited by examiner

Primary Examiner—John Hardee
(74) Attorney, Agent, or Firm—Winston & Strawn

(57) ABSTRACT

Compounds of the formula:

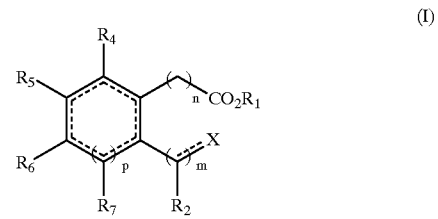

(I)

in which the dotted lines indicate the position of single or double bonds, $R_1$ represents a radical belonging to a fragrant alcohol of the formula $R_1OH$, X represents a nucleophilic group selected from the group consisting of —OH, =O, —NH$_2$ or —NHR$_3$, $R_3$ representing a $C_1$ to $C_6$ straight-chain or branched hydrocarbon radical, saturated or unsaturated, or an aliphatic or aromatic ring having 5 or 6 carbon atoms, m and n define whole numbers within the range 0 to 2 such that the sum m+n is equal to 1 or 2, p defines a whole number with a value of 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated optionally substituted, and, taken two by two, they can form aromatic or aliphatic monocyclic, bicyclic or tricyclic substances with the carbon atoms to which they are bound. Such compounds are capable of releasing a fragrant alcohol of the formula $R_1OH$ upon hydrolysis of the ester bond.

17 Claims, No Drawings

CYCLIC COMPOUNDS AND THEIR USE AS PRECURSORS OF FRAGRANT ALCOHOLS

CROSS-REFERENCE TO RELATED APPLICATIONS

This application is a divisional application of application Ser. No. 09/943,192 filed Aug. 30, 2001 pending, which is a continuation of the U.S. national stage designation of International application PCT/IB00/00315 filed Mar. 21, 2000.

TECHNICAL FIELD

The present invention relates to the perfume industry. More particularly, it is concerned with new cyclic compounds capable of releasing fragrant alcohols.

PRIOR ART

The perfume industry is displaying a particular interest in compounds which are able to prolong a fragrancing effect for a period of time, in particular to mitigate the problems encountered when using volatile perfuming ingredients. Compounds are known which, only under certain conditions of activation such as light, heat, or the presence of enzymes, notably lipases, are capable of releasing a fragrant substance over an extended time period. For example, international patent application WO 95/04809, which belongs to the present applicant, discloses a process for perfuming fabrics washed in the presence of a lipase-containing detergent comprising a compound of formula

The lipase constitutes an activating agent which is necessary to provide the release of a perfuming molecule from the cited compound. These compounds may be used in various applications. The washing of textiles in particular is a field in which scientists are always searching for new means enabling the effect of perfuming substances to be perceived for a period of time after the washing and drying operations. This because many substances which have odours especially suitable for this type of application are known not to be long-lasting on washed items, with the result that their perfuming effect is perceived only briefly. Given the importance of this type of application in the perfume industry, research activity is on-going within this sector, notably with the aim of finding ever more effective solutions to solve the problems mentioned above.

DESCRIPTION OF THE INVENTION

We have now surprisingly discovered the existence of new cyclic compounds that are capable of releasing fragrant alcohols over a long period of time under totally unforeseen and advantageous conditions, that is to say, without any external assistance or activation condition. Thus, contrary to what is known in the prior art, the process of release of a fragrant alcohol by the compounds of the invention does not necessitate the presence of an external catalyst in the reaction medium, for example an enzyme and in particular a lipase. In a textiles-washing application when they are incorporated in a detergent and/or a fabric softener of any kind, these compounds thus enable the characteristic odour of the alcohol to be imparted to the textile and also enable the diffusion effect of this odour to be prolonged so that it develops over a period of time.

The compounds of the invention comply with the following formula,

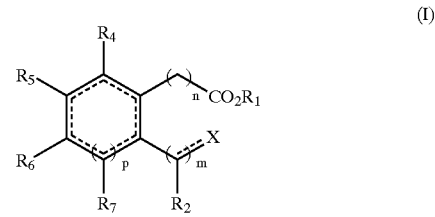

in which the dotted lines indicate the position of single or double bonds, $R_1$ represents a radical belonging to a fragrant alcohol of the formula $R_1OH$, X represents a nucleophilic group selected from the group consisting of —OH, =O, —$NH_2$ or —$NHR_3$, $R_3$ representing a $C_1$ to $C_6$ straight-chain or branched hydrocarbon radical, saturated or unsaturated, or an aliphatic or aromatic ring having 5 or 6 carbon atoms, m and n define whole numbers within the range 0 to 2 such that the sum m+n is equal to 1 or 2, p defines a whole number with a value of 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted and, taken two by two, they can form aromatic or aliphatic monocyclic, bicyclic or tricyclic substances with the carbon atoms to which they are bound.

Of the compounds of formula (I), menthyl-2-acetylbenzoate has been described by H. G. Rule and J. Smith in J. Chem. Soc., 1926, 553 and by L. Homer and J. Klaus in Liebigs Ann. Chem., 1979, 1232. Similarly, menthyl 2-formylbenzoate has been described by M. V. Bhatt et al. in J. Org. Chem., 1977, 42, 2697, benzyl 2-formylbenzoate has been described by N. Gautier and R. H. Dodd in Synth. Commun., 1998, 28, 3769, octyl 2-formylbenzoate by J. Barry et al., Synthesis, 1985, 40, and finally benzyl 2-acetylbenzoate by A. Kotali et al., Org. Prep. Proced. Int., 1996, 28, 622. However, these documents of the prior art contain no mention, description or suggestion of any use of these compounds in perfumery, in particular as precursors susceptible of releasing fragrant alcohols.

The compounds of the invention are capable of releasing a fragrant alcohol of the formula $R_1OH$ on hydrolysis of their ester bond. Fragrant alcohol here means an alcohol of current use in perfumery, that is to say, one which is useable as a perfuming ingredient for the preparation of perfumes or perfumed articles. The criteria to be met as a useable perfuming ingredient are known to the person skilled in the art and include, notably, a certain originality of the fragrance, stability, or even a favourable cost/effectiveness ratio. Although it is obviously impossible to provide an exhaustive list of known alcohols of the formula $R_1OH$ which may be used according to the invention, we mention by way of example anisyl alcohol, fenchyl alcohol, cinnamic alcohol, 9decen-1-ol, phenethylol, citronellol (3,7-dimethyl-6-octen-1-ol), 3-methyl-5-phenyl-1-pentanol (source: Firmenich S. A., Geneva, Switzerland), Mayol® (7p-menthan- 1-ol; source: Firmenich S. A., Geneva, Switzerland), dihydromyrcenol (2,6-dimethyl-oct-7-ene-2-ol), alpha-ionol, tetrahydro-ionol, geraniol [(E)-3,7-dimethyl-2,6-octadien-1-ol], nerol (Z)-3,7-dimethyl-2-6-octadien-1-ol, (Z)-3-hexen-1-ol, 1-hexanol, 2-hexanol, 3,3,5-trimethylhexanol, 3,4,5,6,6-pentamethyl-heptan-2-ol, 5-ethyl-2-nonanol, (Z)-6-nonenol, 6,8-dimethyl-2-nonanol, 2,6-nonadien-1-ol, borneol, 1-octen-3-ol, 4-cyclohexyl-2-methyl-2-butanol (source: Firmenich S. A., Geneva, Switzerland), 6-ethyl-3-methyl-5-octen-1-ol, 3,7-dimethyl-oct-3,6-dienol, 7-methoxy-3,7-dimethyl-octan-2-ol, methyl-4-phenyl-2-butanol, 2-methyl-1-phenyl-2-propanol, 1-phenylethanol, 2-phenylethanol, 2-phenylpropanol, 3-phenylpropanol, 2-methyl-5-phenylpentanol, 2-methyl-4-phenylpentanol, 3-methyl-5-phenylpentanol, cyclomethyl-citronellol, decanol, dihydroeugenol, 8-p-methanol, 3,7-dimethyl-1-octanol, 2,6-dimethyl-2-heptanol, dodecanol, octanol, undecanol, 4-methyl-3-decen-1-ol, eugenol, Florol® (tetrahydro-2-isobutyl-4-methyl-4 (2H)-pyranol; source: Firmenich S. A., Geneva, Switzerland), 2-phenoxy-ethanol, isoeugenol, linalol, Tarragol® (2-methoxy-4-propyl-1-cyclohexanol; source: Firmenich S. A., Geneva, Switzerland), vanillin, ethyl-vanillin, anethol, famesol, cedrenol, menthol, p-menth-8-en-3-ol, 3,3,5-trimethyl-cyclohexanol, 2,4,6-trimethyl-3-cyclohexenyl-methanol, 4-(1-methylethyl) cyclohexyl-methanol, terpineol, tetrahydromugol, 3,7-dimethyl-3-octanol, Polysantol® (E)-3,3-dimethyl-5-(2',2',3'-trimethyl-3'-cyclopenten-1-yl)-4-penten-2-ol; source: Firmenich S. A., Geneva, Switzerland), 2,2,6-trimethyl-alpha-propyl-cyclohexane propanol, 5-(2,2,3-trimethyl-3-cyclopentyl)-3-methylpentan-2-ol, 3-methyl-5-(2,2,3-trimethylcyclopent-3-enyl)pent-4-en-2-ol, 2-ethyl-4-(2,2,3-trimethylcyclopent-3-enyl) but-2-en-1-ol, 4-(5,5,6-trimethylbicyclo[2.2.1]hept-2-yl)-cyclohexanol, 2-(2-methyl-propyl)4-hydroxy-4-methyl-tetrahydropyrane, 2-cyclohexyl propanol, 2-(1,1-dimethyl-ethyl)-4-methyl-cyclohexanol, 1-(2-tert-butyl-cyclo hexyloxy)-2-butanol, 1-(4-isopropyl-cyclohexyl)-ethanol, Limbanol® [1-(2,2,3,6-tetramethyl-cyclohex-1-yl)-3-hexanol; source: Firmenich S. A., Geneva, Switzerland), 1-heptanol, 1-nonanol and 10-undecen-1-ol. It goes without saying that this list is not complete, any alcohol capable of imparting an odour to a product to be perfumed being comprised in the alcohols of formula $R_1OH$ related to the invention.

The characteristic feature of the invention resides in the fact that the hydrolysis which induces the release of alcohol is facilitated by an auxiliary effect of the ester bond's neighbouring nucleophilic group X. This effect provides a totally unexpected advantage, that is, it permits cleavage of the ester bond by hydrolysis under simple alkaline conditions, as shown diagrammatically below:

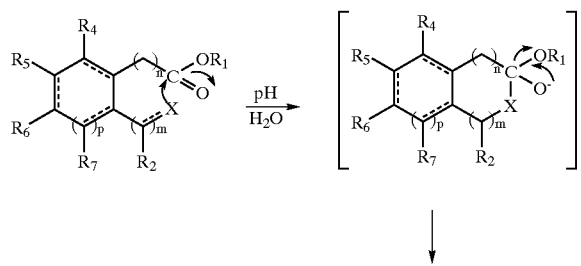

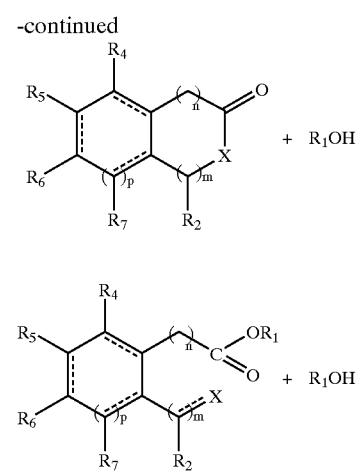

Examples are the conventional conditions of textiles washing, in the course of which a change in pH occurs. The pH passes from a value corresponding to an acid medium to values corresponding to a neutral or even a basic medium during the washing cycle, thus enabling the compounds of the invention to be hydrolysed.

Otherwise the reaction is catalysed naturally in the presence of heat. This occurs for example when washing is dried, namely in a tumble-dryer. The hydrolysis reaction leads to the formation of an odoriferous substance $R_1OH$ wherein $R_1$ has the meaning indicated above, and of a residue of the initial precursor, which is generally odourless.

The reaction requires no activation condition such as the presence of a lipase in the detergent, as reported in the prior art (WO 95/04809).

We also noticed that the preferred compounds according to the invention exhibit a common characteristic enabling them to benefit from this auxiliary effect of the neighbouring group for hydrolysis of the ester bond. The compounds claimed are in fact capable of assuming a constrained conformation in which the distance between the oxygen or nitrogen of the nucleophilic group X and the carbon of the ester function does not exceed 2.8 Angström for a molecular energy calculated by the method MM2 (molecular mechanical) which differs by no more than 3 kcal/mol from the minimum total energy of the molecule.

"Constrained conformation" is here understood to mean a conformation different from the most stable conformation of the molecule and the achievement of which requires a specific quantity of energy relative to the minimum energy of the molecule, that is, the energy of the molecule in its most stable conformation. The respective molecular energy values are molecular parameters established for each compound with the aid of a model SGI R10000 computer using a MacroModel V6.5 programme (F. Mohamadi et al., J. Comput. Chem. 1990, 11, 440). The minimum total energies are obtained by the method known from the prior art, designated by method MM2 and by the Monte Carlo procedure executed on MacroModel. The energies of the constrained conformations are defined in accordance with the same method. We were surprised to discover that the compounds exhibiting the above-mentioned distance and energy constraints were capable of prolonged release of the fragrant alcohol $R_1OH$ over time and under the normal conditions of application, i.e. when these compounds are used in the treatment of textiles or various other surfaces.

Amongst the compounds of the invention according to formula (I) in which X represents an =O group, the 2-acyl-benzoates of the formula

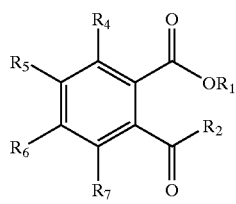

are appreciated.

Preferentially one may cite 3,7-dimethyl-6-octenyl 2-formylbenzoate, (E or Z)-3,7-dimethyl-2,6-octadienyl 2-formylbenzoate, 2-phenylethyl 2-formylbenzoate, (E)-3,7-dimethyl-2,6-octadienyl 2-acetylbenzoate, 3,7-dimethyl-6-octenyl 2-acetylbenzoate, and (1R, 3R, 4S)-3-menthanyl 2-acetylbenzoate. Of the preferred compounds defined above, the ones most preferred are 3,7-dimethyl-6-octenyl 2-formylbenzoate, (E)-3,7-dimethyl-2,6-octadienyl 2-formylbenzoate, phenylethyl 2-formylbenzoate and (E)3,7-dimethyl-2,6-octadienyl 2-acetylbenzoate.

On the other hand, the preferred compounds among those of the invention of formula (1) in which X defines an —OH group are the 2-hydroxymethylbenzoates and the esters of dihydrocoumaric acid, of the respective formulae

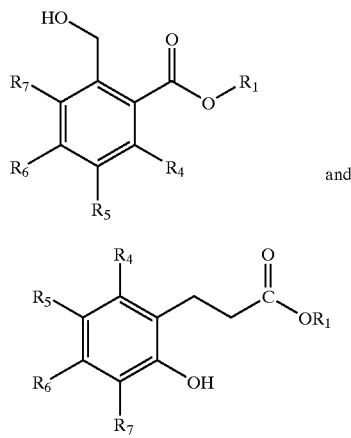

One may cite in particular a preference for 3-p-menthanyl 2-hydroxy-methylbenzoate, 3,7-dimethyl-6-octenyl 2-hydroxymethylbenzoate, 2-phenyl-ethyl 2-hydroxymethylbenzoate, (Z)-3-hexenyl 2-hydroxymethylbenzoate, (E)-3,7-dimethyl-2,6-octadienyl 2-hydroxymethylbenzoate, 1-p-menthen-8-yl 2-hydroxymethylbenzoate, (1'R,E)-1,2,2-trimethyl-4 (2',2',3'-trimethyl-3'-cyclopenten-1'-yl)-3-butenyl 2-hydroxy-methylbenzoate, (Z)-3-hexenyl dihydrocoumarate, (E)-3,7-dimethyl-2,6-octa-dienyl dihydrocoumarate and (Z)-3-hexenyl 3-endo-hydroxymethyl-bicyclo[2.2.1]hept-5-ene-2-endo-carboxylate.

The compounds of the invention may be prepared starting from commercially available compounds and with the aid of conventional methods. Thus in a general way, starting with commercially available starting materials (acids or anhydrides) an ester bond is produced by conventional esterification of carboxyls, or by acid catalysis. Then, if necessary, the residual function (acid, aldehyde or ketone) corresponding to the future nucleophilic function is functionalised by reduction or reductive amination depending on the precursor required.

For example, the 2-acyl- and 2-formyl-benzoates are prepared on the basis of corresponding acids by simple esterification according to the following scheme:

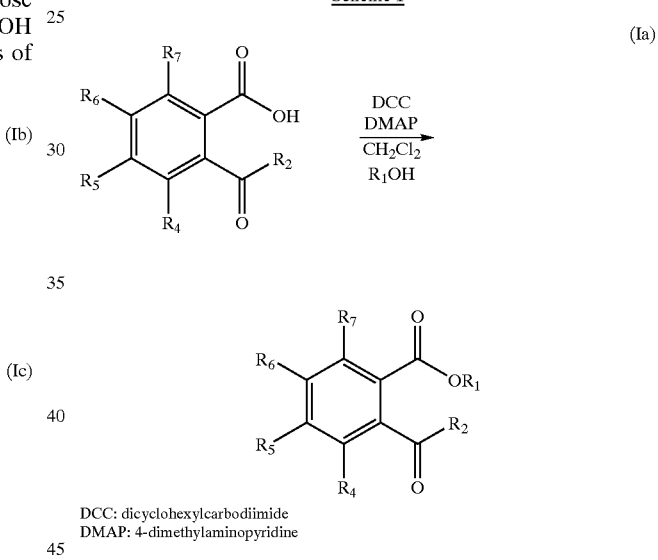

DCC: dicyclohexylcarbodiimide
DMAP: 4-dimethylaminopyridine

Other compounds such as the 2-hydroxymethylbenzoates may be prepared from the corresponding phthalates, as shown in the scheme below:

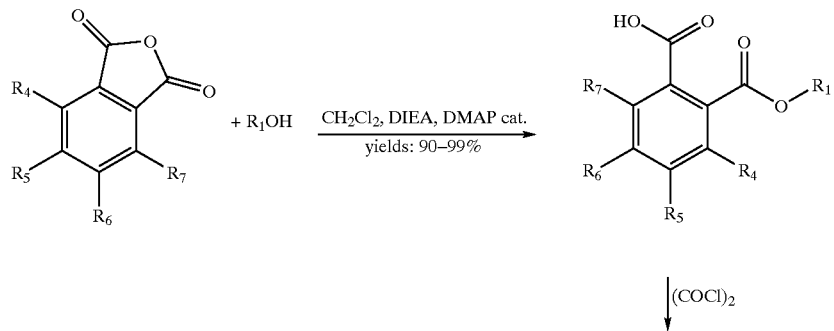

-continued

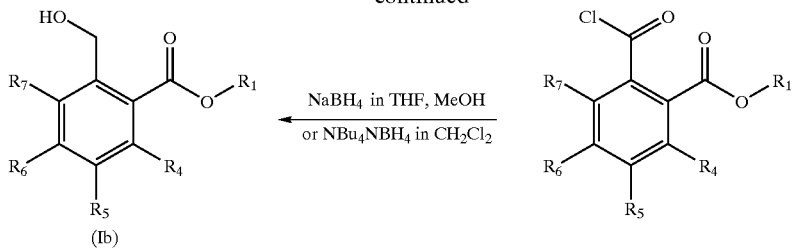

(Ib)

DIEA: diisopropylethylamine
DMAP: 4-dimethylaminopyridine
(COCl$_2$): oxalyl chloride
NaBH$_4$: sodium boron hydride
THF: tetrahydrofurane
Bu$_4$NBH$_4$: tetrabutylammonium boron hydride According to another example, esters of dihydrocoumaric acid may be prepared from o-coumaric acid as follows:

Scheme 3

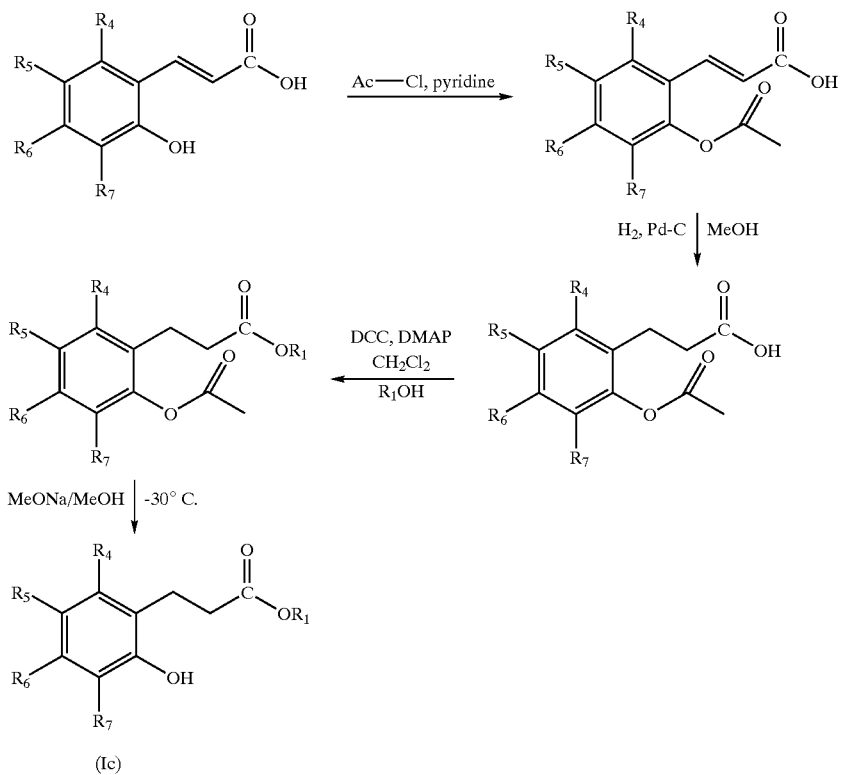

(Ic)

AcCl: acetyl chloride
DCC: dicyclohexylcarbodiimide
DMAP: 4-dimethylaminopyridine All the symbols used in the above diagrams have the meaning indicated in formula (I).

The compounds according to the invention lend themselves to any application requiring the prolonged-release effect of an odoriferous compound as defined above. They are used in particular in functional perfumery, notably in applications such as liquid or solid detergents intended for the treatment of textiles and textile softeners, for which one seeks ingredients the odours of which, once imparted to the textile during washing, can be perceived by the consumer over a period of several days thereafter. The invention enables the odoriferous effect of the above-mentioned alcohols, and thus the "freshness" of the washing, to be prolonged for several days.

The compounds of the invention may be used as perfuming ingredients for the washing in all types of detergent or softening base in which these compounds are stable. By way of example, detergents of the type of those described in the patent WO 97/34986 may be used. Moreover, as softening bases one may select those described in the patents U.S. Pat. Nos. 4,137,180, 5,236,615, or EP 799 885. Other typical compositions of detergents and softeners which may be used are described in works such as Ullmann's Encyclopedia of Industrial Chemistry, vol. A8, pages 315448 (1987) and vol. A25, pages 747–817 (1994); E. W. Flick, Advanced Cleaning Product Formulations, Noyes Publication Park Ridge, N.J. (1989); M. S. Showell (Ed.), in Surfactant Science Series, vol. 71; Powered Detergents, Marcel Dekker, New York, N.Y. (1998); Proceedings of the 4*th* World Conference on Detergents: Strategies for the 21*st* century, A. Cahn (Ed), AOCS Presse, Champaign (1998).

Of course, the use of the compounds of the invention is not limited to the products mentioned above. These compounds lend themselves equally to all the other uses current in the perfume industry, that is to say, to the perfuming of shower or bath soaps and gels, of foam baths, of products for the treatment or hygiene of hair such as shampoos, as well as body deodorants and air fresheners and also cosmetic preparations. In the applications such as shower or bath soaps and gels, foam baths or shampoos, a neutral or even basic pH capable of inducing hydrolysis of the ester bond and thus release of a fragrant alcohol, may be reached for instance as the result of a high dilution of the base in water.

The compounds may also be employed in applications such as detergent compositions or cleaning materials for washing the dishes or various surfaces, whether intended for domestic or industrial use.

In these applications they may be used on their own, mixed together, or in mixtures with other perfuming ingredients, solvents or adjuvants currently used in perfumery. The nature and variety of these co-ingredients do not require a more detailed description here. In any case, this could not be exhaustive, as the person skilled in the art is able to select them on the basis of his or her general knowledge, and depending on the nature of the product to be perfumed and the required olfactory effect. These perfuming ingredients belong to classes of chemicals as varied as alcohols, aldehydes, ketones, esters, ethers, acetates, nitrites, terpene hydrocarbons, nitrogenous or sulphurous heterocyclic compounds, as well as essential oils of natural or synthetic origin. Many of these ingredients are moreover indexed in reference texts such as S. Arctander's book, Perfume and Flavor Chemicals, 1969, Montclair, N.J., USA, or its more recent editions, or in other works of a similar nature.

The proportions in which the compounds according to the invention may be incorporated into the different products mentioned above vary within an extensive range of values. These values depend on the nature of the article or product to be perfumed and the required olfactory effect, as well as on the nature of the co-ingredients in a given composition when the compounds of the invention are used in mixtures with perfuming co-ingredients, solvents or adjuvants currently used in the art.

By way of example one may cite typical concentrations of the order of 0.1 to 5%, or more, by weight of these compounds relative to the weight of the composition in which they are incorporated. Concentrations below these may be used when these compounds are directly applied to the perfuming of the various consumer products mentioned above.

The invention will now be described in more detail in the following examples, in which the temperatures are given in degrees Celsius, the coupling constants (J) are given in Hertz and the abbreviations have the conventional meaning in the art.

Embodiments of the Invention

EXAMPLE 1

Preparation of the Formula (I) Compounds a) 3,7-Dimethyl-6-octenyl 2-formylbenzoate A solution of 7.50 g (50.0 mmol) 2-formylbenzoic acid, 4.88 g (40.0 mmol) 4-dimethyl aminopyridine (DMAP) and 15.60 g (100.0 mmol) citronellol in 75 ml dichloromethane was cooled in an ice bath before addition of a solution of 11.35 g (55.0 mmol) dicyclohexylcarbodiimide (DCC) in 25 ml dichloromethane for 15 min. The reaction medium was maintained with stirring at 0° for 15 min, then at 20° for 48 h. The precipitate formed during the reaction was filtered and the filtrate washed with HCl (10%, 2×) and with a saturated $Na_2CO_3$ solution (2×). The organic phase was dried over $Na_2SO_4$, concentrated and chromatographed twice ($SiO_2$, ethyl toluene/ethyl acetate 19:1 and $SiO_2$, toluene) to give 2.25 g (16%) 3,7 dimethyl-6-octenyl 2-formylbenzoate in the pure state in the form of a colourless oil.

Analytical Data:

UV/Vis (hexane): 288 (1400), 241 (8500).

IR(neat): 2960m, 2924m, 2854m, 2117m, 1774w, 1713s, 1697s, 1594m, 1577w, 1449m, 1379m, 1359w, 1346w, 1302w, 1264s, 1192m, 1162w, 1131m, 1077s, 1043w, 985w, 947w, 890w, 821m, 800w.

$^1$H-NMR(360 MHz, $CDCl_3$): 10.63 (s, 1H), 8.00-7.90 (m, 2H), 7.70-7.60 (m, 2H), 5.15-5.05 (m, 1H), 4.50-4.36 (m, 2H), 2.12-1.92 (m, 2H), 1.92-1.78 (m, 1H),1.78-1.52 (m, 2H), 1.67 (s, 3H), 1.60 (s, 3H), 1.48-1.34 (m, 1H), 1.34-1.17 (m, 1H), 0.98 (d, J=6.3, 3H).

$^{13}$C NMR(90.6 MHz, $CDCl_3$): 192.06 (d); 166.33 (s); 137.10 (s); 132.89 (d); 132.45 (s); 132.26 (d); 131.46 (s); 130.31 (d), 128.35 (d); 124.45 (d); 64.49 (t); 36.94 (t); 35.44 (t); 29.53 (d); 25.70 (q); 25.37 (t); 19.46 (q); 17.66 (q).

MS(EI): 151 (20), 150 (15), 149 (89), 140 (3), 139 (4), 138 (41), 137 (21), 135 (2), 134 (17), 133 (100), 132 (12), 125 (2), 124 (5), 123 (53), 122 (5), 121 (7), 112 (2), 111 (6), 110 (6), 109 (24), 106 (4), 105 (37), 104 (32), 97 (4), 96 (15), 95 (73), 94 (7), 93 (10), 84 (7), 83 (17), 82 (58), 81 (93), 80 (9), 79 (5), 78 (3), 77 (36), 76 (17), 75 (3), 74 (2), 71 (5), 70 (26), 69 (91), 68 (27), 67 (49), 66 (2), 65 (12), 57 (12), 56 (15), 55 (46), 54 (4), 53 (12), 52 (2), 51 (17), 50 (7), 43 (12), 42 (10), 41 (98), 40 (3), 39 (17), 29 (14), 27 (11).

b) (E)-3,7-Dimethyl-2,6-octadienyl 2-formylbenzoate

A solution of 7.50 g (50.0 mmol) 2-formylbenzoic acid, 4.89 g (40.0 mmol) DMAP and 15.42 g (100.0 mmol) geraniol in 75 ml dichloromethane was cooled in an ice bath before addition of a solution of 11.37 g (55.0 mmol) DCC in 25 ml dichloromethane, for 15 min. The reaction medium was maintained under stirring at 0° for 15 min, then at 20° for 48 h. The precipitate formed during the reaction was filtered and the filtrate washed with HCl (10%, 2×) and with a saturated $Na_2CO_3$ solution (2×) and water (2×). The organic phase was dried over $Na_2SO_4$, concentrated and chromatographed ($SO_2$, 8:2 heptane/ether) to give 2.55 g (22%) (E)3,7-dimethyl-2,6-octadienyl 2-formylbenzoate in the pure state in the form of a colourless oil.

Analytical Data:

UV/Vis (hexane): 288 (1400), 241 (9000), 209 (36800).

IR (neat): 2967w, 2914m, 2853w, 1777w, 1711s, 1695s, 1594m, 1577m, 1484w, 1446m, 1376m, 1340w, 1303w, 1253s, 1191m, 1162w, 1128m, 1071s, 1040w, 963w, 924m, 890w, 819m, 799w, 748s, 699m, 639m.

$^1$H-NMR (360 MHz, $CDCl_3$): 10.63 (s, 1H); 8.01-7.90 (m, 2 H); 7.68-7.60 (m, 2 H);

5.52-5.45 (m, 1H); 5.13-5.05 (m, 1H); 4.90 (d, J=7.5, 2 H); 2.18-2.03 (m, 4 H); 1.78 (s, 3 H); 1.67 (s, 3 H); 1.61 (s, 3 H).

$^{13}$C-NMR (90.6 MHz $CDCl_3$): 192.14 (d); 166.34 (s); 143.48 (s); 136.99 (s); 132.91 (d); 132.57 (s); 132.23 (d); 131.95 (s); 130.41 (d); 128.31 (d); 123.63 (d); 117.73 (d); 62.75 (t); 39.55 (t); 26.26 (t); 25.68 (q); 17.71 (q); 16.59 (q).

MS (EI): 151 (8), 150 (3), 149 (29), 137 (3), 136 (20), 135 (3), 134 (12), 133 (51), 123 (4), 122 (5), 121 (20), 107 (7), 106 (4), 105 (18), 104 (4), 95 (8), 94 (9), 93 (40), 92 (11), 91 (5), 81 (10), 80 (19), 79 (7), 78 (3), 77 (20), 76 (6), 70 (7), 69 (100), 68 (60), 67 (24), 65 (8), 55 (7), 53 (12), 51 (11), 50 (5), 43 (5), 42 (4), 41 (80), 39 (14), 29 (7), 21 (9).

In the same way we prepared (Z)-3,7-dimethyl-2,6-octadienyl 2-formylbenzoate using 15.0 g (100 mmol) 2-formylbenzoic acid, 9.76 g (80 mmol) DMAP and 30.84 g (200 mmol) nerol in 150 ml dichloromethane and 22.70 g (110.0 mmol) DCC in 50 ml dichloromethane. Column chromatography ($SiO_2$, toluene) of 2×5 g of the crude product gave 1.58 g (corresponding to a total yield of 24%) of the pure product.

Analytical Data:

UV/Vis (hexane): 287 (1000), 278 (sh, 900), 240 (6400), 232 (sh, 6100), 208 (sh, 27100).

IR (neat): 2964m, 2913m, 2856m, 1777m, 1710s, 1696s, 1594m, 1577m, 1483w, 1447m, 1376m, 1358w, 1347w, 1304w, 1254s, 1192m, 1162w, 1128m, 1071m, 1040m, 1010w, 983w, 923m, 894w, 819m, 799w, 748s, 713w, 700m, 688w.

$^1$H-NMR (360 MHz, $CDCl_3$): 10.63 (s, 1H); 8.02-7.90 (m, 2 H); 7.68-7.59 (m, 2 H); 5.49 (t, J=7.3, 1 H); 5.16-5.07 (m, 1H); 4.87 (d, J=7.5, 2 H); 2.25-2.00 (m, 4 H); 1.80 (s, 3 H); 1.67 (s, 3 H); 1.60 (s, 3 H).

$^{13}$C-NMR (90.6 MHz, $CDCl_3$): 192.17 (d); 166.30 (s); 143.64 (s); 136.99 (s); 132.91 (d); 132.52 (s); 132.35 (s), 132.24 (d); 130.41 (d); 128.31 (d); 123.45 (d); 118.58 (d); 62.49 (t); 32.24 (t); 26.63 (t); 25.69 (q); 23.55 (q); 17.68 (q).

MS (EI): 153 (5), 151 (13), 150 (8), 149 (60), 137 (6), 136 (33), 135 (6), 134 (21), 133 (95), 123 (6), 122 (7), 121 (36), 108 (3), 107 (12), 106 (4), 105 (24), 104 (4), 95 (13), 94 (14), 93 (79), 92 (18), 91 (8), 82 (3), 81 (19), 80 (31), 79 (8), 78 (3), 77 (22), 76 (6), 70 (7), 69 (100), 68 (59), 67 (24), 65 (8), 55 (5), 53 (13), 51 (8), 50 (3), 43 (5), 41 (39), 39 (7).

c) 2-Phenylethyl 2-formylbenzoate

A solution of 12.72 g (84.8 mmol) 2-formylbenzoic acid, 8.27 g (67.8 mmol) DMAP and 20.69 g (169.6 mmol) 2-phenylethanol in 130 ml dichloromethane was cooled in an ice bath before adding a solution of 19.25 g (93.3 mmol) DCC in 40 ml dichloromethane for 10 min. The reaction medium was maintained under stirring at 0° for 15 min, then at 20° for 48 h. The precipitate formed during the reaction was filtered and the filtrate washed with HCl (10%, 2×) and with a saturated $Na_2CO_3$ solution (2×) and with water (2×). The organic phase was dried over $Na_2SO_4$, concentrated and chromatographed ($SiO_2$, 8:2 heptane/ether) to give 2.38 g (11%) 2-phenylethyl 2-formylbenzoate in the pure state in the form of a colourless oil.

Analytical Data:

UV/Vis (hexane): 336 (28), 288 (1400), 241 (8400), 209 (37700).

IR (neat): 3064w, 3026w, 2953w, 2893w, 1712s, 1692s, 1593m, 1577m, 1496m, 1483w, 1465w, 1452m, 1382m, 1264s, 1253s, 1191m, 1163w, 1126s, 1075m, 1040m, 1030m, 989m, 961m, 908w, 891w, 863w, 818m, 799m, 746s, 698s.

$^1$H-NMR (360 MHz, $CDCl_3$): 10.50 (s, 1H); 7.95-7.86 (m, 2 H); 7.66-7,57 (m, 2 H); 7.37-7.30 (m, 2 H); 7.30-7.22 (m, 3 H); 4.60 (t, J=6.9, 2 H); 3.10 (t, J=6.9, 2H).

$^{13}$C-NMR (90.6 MHz, $CDCl_3$): 192.06 (d); 166.17 (s); 137.44 (s); 137.04 (s); 132.91 (d); 132.35 (d); 132.18 (s); 130.34 (d); 128.92 (d); 128.65 (d); 128.35 (d); 126.79 (d); 66.36 (t); 35.08 (t).

MS (EI): 236 (1), 150 (3), 149 (27), 134 (3), 133 (23), 121 (3), 106 (5), 105 (35), 104 (100), 93 (2), 91 (8), 79 (6), 78 (7), 77 (18), 76 (5), 65 (5), 51 (7), 50 (3), 39 (2).

This product was also prepared with a yield of 14% from 2-formylbenzoic acid and 2-bromoethylbenzene in acetone in the presence of potassium carbonate.

d) (E)-3,7-Dimethyl-2,6-octadienyl 2-acetylbenzoate

A solution of 6.49 g (39.0 mmol) 2-acetylbenzoic acid, 3.81 g (31.2 mmol) DMAP and 12.32 g (80.0 mmol) geraniol in 60 ml dichloromethane was cooled in an ice bath before adding a solution of 8.84 g (42.9 mmol) DCC in 40 ml dichloromethane for 5 min. The reaction mixture was maintained with stirring at 40° for 75 h. The precipitate formed during the reaction was filtered and the filtrate washed with HCl (10%, 2×) and with a saturated $Na_2CO_3$ solution (2×). The organic phase was dried ($Na_2SO_4$) and concentrated. The excess geraniol was distilled, and the residue chromatographed ($SiO_2$, 9:1 toluene/ethyl acetate) to give 9.08 g (78%) of the desired compound in the form of a slightly yellow oil.

Analytical Data:

UV/Vis (hexane): 313 (sh, 200), 300 (sh, 200), 282 (sh, 900), 276 (900), 268 (1000), 228 (9200).

IR(neat): 2966w, 2920m, 2856w, 1784w, 1715s, 1704s, 1673w, 1597w, 1574w, 1494w, 1484w, 1445m, 1376m, 1354m, 1263s, 1205w, 1163w, 1137m, 1126m, 1100m, 1062m, 1038w, 1006w, 955m, 931m, 886w, 834w, 799w, 761m, 731m, 708m, 696m, 661w.

$^1$H-NMR(360 MHz, $CDCl_3$): 7.90-7.84 (m, 1H), 7.55 (ddd, J=7.5, 7.5, 1.2, 1H), 7.48 (ddd, J=7.5, 7.5, 1.2, 1H), 7.39 (dd, J=7.5, 1.6, 1H), 5.49-5.41 (m, 1H), 5.13-5.05 (m, 1H), 4.83 (d, J=7.5, 2H), 2.53 (s, 3H), 2.20-1.95 (m, 4H), 1.75 (s, 3H), 1.67 (s, 3H). 1,60 (s, 3H).

$^{13}$C NMR(90.6 MHz, $CDCl_3$): 203.01 (s), 166.92 (s), 143.12 (s), 142.94 (s), 131.95 (d), 131.85 (s), 129.91 (d), 129.78 (d), 129.09 (s), 128.23 (s), 126.36 (d), 123.73 (d), 117.75 (d), 62.51 (t), 39.55 (t), 30.17 (q), 26.31 (t), 25.66 (q), 17.69 (q), 16.54 (q).

MS(EI): 166 (2), 165 (23), 153 (1), 150 (1), 149 (6), 148 (28), 147 (100), 146 (8), 137 (3), 136 (26), 135 (1), 129 (1), 123 (3), 122 (2), 121 (19), 120 (1), 119 (1), 118 (2), 109 (1), 108 (2), 107 (6), 106 (1), 105 (11), 104 (6), 103 (1), 97 (1), 96 (1), 95 (4), 94 (11), 93 (33), 92 (10), 91 (20), 90 (2), 89 (2), 85 (1), 84 (1), 83 (1), 82 (1), 81 (5), 80 (13), 79 (6), 78 (1), 77 (8), 76 (7), 75 (1), 74 (1), 71 (1), 70 (3), 69 (46), 68 (42), 67 (15), 66 (1), 65 (4), 63 (1), 59 (1), 55 (3), 54 (1), 53 (6), 52 (1), 51 (2), 50 (2), 43 (6), 42 (2), 41 (22), 40 (1), 39 (4), 29 (1), 27 (2).

e) 3,7-Dimethyl-6-octenyl 2-acetylbenzoate

A solution of 6.49 g (30.0 mmol) 2-acetylbenzoic acid, 3.81 g (31.2 mmol) DMAP and 12.48 g (80.0 mmol) citronellol in 60 ml dichloromethane was cooled in an ice bath before adding a solution of 8.84 g (42.9 mmol) DCC in 40 ml dichloromethane over 5 min. The reaction mixture was maintained with stirring at 40° for 75 h. The precipitate formed during the reaction was filtered and the filtrate washed with HCl (10%, 2×) and with a saturated $Na_2CO_3$ solution (2×). The organic phase was dried ($Na_2SO_4$), and the solvent-evaporated. The excess citronellol was distilled (1 Torr, 60–80°), and the residue chromatographed ($SiO_2$, 9:1 toluene/ethyl acetate) and distilled (0.6 Torr, 150–155°), to give 7.43 g (63%) of 3,7-dimethyl-6-octenyl 2-acetylbenzoate in the form of a colourless oil.

Analytical Data:

UV/Vis (hexane): 313 (sh, 100), 281 (sh, 1000), 276 (1000), 229 (9000).

IR(neat): 2961m, 2913m, 2872w, 2855w, 1717s, 1704s, 1597w, 1574w, 1446m (broad), 1378w, 1354m, 1264s, 1248m, 1129m, 1100m, 1064m, 1038w, 1007w, 956m, 884w, 835w, 801w.

$^1$H-NMR(360 MHz, $CDCl_3$): 7.86 (dd, 3=7.5, 1.2, 1H), 7.56 (ddd, J=7.5, 7.5, 1.2, 1H), 7.49 (ddd, J=7.5, 7.5, 1.6, 1H), 7.40 (dd, J=7.5, 1.2, 1H), 5.14-5.05 (m, 1H), 4.42-4.27

(m, 2H), 2.54 (s, 3H), 2.18-2.12 (m, 2H), 1.87-1.72 (m, 1H), 1.72-1.48 (m, 2H), 1.67 (s, 3H), 1.60 (s, 3H), 1.46-1.32 (m, 1H), 1.29-1.15 (m, 1H), 0.95 (d, J=6.3, 3H).

$^{13}$C NMR(90.6 MHz, CDCl$_3$): 202.93 (s); 166.97 (s); 142.92 (s); 131.95 (d); 131.35 (s); 129.92 (d); 129.70 (s); 129.09 (s); 126.36 (d); 124.54 (d); 64.25 (t); 36.97 (t); 35.29 (t); 30.13 (q); 29.49 (d); 25.70 (q); 25.38 (t); 19.40 (q); 17.65 (q).

MS(EI): 166 (2), 165 (23), 149 (12), 148 (19), 147 (100), 146 (41), 139 (2), 138 (18), 137 (3), 124 (3), 123 (28), 118 (6), 110 (3), 109 (13), 105 (7), 104 (18), 96 (6), 95 (30), 94 (2), 93 (2), 91 (13), 90 (9), 89 (5), 83 (5), 82 (21), 81 (33), 80 (3), 79 (2), 77 (5), 76 (14), 75 (3), 74 (3), 71 (4), 70 (4), 69 (26), 68 (8), 67 (16), 65 (2), 63 (2), 57 (2), 56 (4), 55 (11), 53 (3), 50 (4), 43 (5), 42 (2), 41 (15), 39 (3).

f) (1R, 3R, 4S)-3-p-Menthanyl 2-acetylbenzoate

A solution of 11.36 g (50.0 mmol) 2-acetylbenzoic acid, 4.88 g (40.0 mmol) DMAP and 23.40 g (150.0 mmol) (−)-menthol in 80 ml dichloromethane was cooled in an ice bath before adding a solution of 11.36 g (55.0 mmol) DCC in 40 ml dichloromethane for 15 min. The reaction mixture was maintained with stirring at 40° for 70 h. The precipitate formed during the reaction was filtered and the filtrate washed with HCl (10%, 2×) then with a saturated Na$_2$CO$_3$ solution (2×). The organic phase was dried (Na$_2$SO$_4$), concentrated, chromatographed (SiO$_2$, toluene) and recrystallised in hexane to give 1.96 g (13%) (1R, 3R, 4S)-3-p-menthanyl 2-acetylbenzoate in the form of white crystals.

Analytical Data:

M.p.: 89–91° C.

UV/Vis (hexane): 315 (sh, 100), 281 (sh, 900), 275 (1000), 229 (9700).

IR(neat): 3068w, 2962m, 2951m, 2924m, 2914m, 2865m, 2847m, 1716s, 1686s, 1593w, 1576w, 1488w, 1455m, 1417w, 1385w, 1360m, 1335w, 1284m, 1272s, 1259s, 1183w, 1154w, 1139m, 1106m, 1095m, 1080w, 1064m, 1035m, 1016w, 980m, 954s, 914m, 884w, 838w.

$^1$H-NMR(360 MHz, CDCl$_3$): 7.87 (dd, J=7.7, 1.4, 1H), 7.55 (ddd, J=7.5, 7.5, 1.6, 1H), 7.48 (ddd, J=7.5, 7.5, 1.6, 1H), 7.38 (dd, J=7.5, 1.2, 1H), 4.93 (ddd, 3=11.0, 11.0, 4.3, 1H), 2.54 (s, 3H), 2.21-2.12 (m, 1H), 2.02-1.88 (m, 1H), 1.78-1.67 (m, 2H), 1.63-1.44 (m, 2H), 1.20-1.03 (m, 2H), 1.00-0.85 (m, 1H), 0.94 (d, J=6.7, 3H), 0.92 (d, J=7.1, 3H), 0.80 (d, J=6.7, 3H).

$^{13}$C NMR(90.6 MHz, CDCl$_3$): 203.20 (s), 143.20 (s), 131.92 (d), 129.76 (d), 129.64 (d), 129.26 (s), 126.23 (d), 75.84 (d), 47.16 (d), 40.59 (t), 34.25 (t), 31.49 (d), 30.35 (q), 26.30 (d), 23.42 (t). 22.02 (q), 20.81 (q), 16.26 (q).

MS(EI): 303 ([M+1]$^+$, 1): 166 (4), 165 (37), 150 (1), 149 (9), 148 (32), 147 (100), 146 (3), 139 (6), 138 (23), 137 (2), 124 (1), 123 (10), 117 (1), 111 (1), 105 (6), 104 (4), 97 (2), 96 (5), 95 (20), 94 (2), 93 (1), 92 (1), 91 (13), 90 (1), 89 (1), 84 (1), 83 (9), 82 (5), 81 (13), 80 (1), 79 (2), 78 (1), 77 (3), 76 (4), 75 (1), 71 (1), 69 (4), 68 (1), 67 (3), 65 (2), 57 (2), 56 (1), 55 (6), 54 (1), 53 (1), 51 (1), 50 (1), 43 (4), 41 (3), 39 (1).

g) (1R, 3R, 4S)-3-p-Menthanyl 2-hydroxymethylbenzoate 3.78 g (12.4 mmol) monomenthyl (−)-phthalate (Fluka) was heated at reflux in 19 ml oxalyl chloride (18 eq.) for 1.5 h. The excess oxalyl chloride was distilled under vacuum. 2.75 g crude acid chloride was then diluted in 5 ml THF cooled to −80 under argon, and 0.97 g (3 eq.) NABH$_4$ was added. The reaction mixture was maintained under stirring at 0° for 10 min and at ambient temperature for 30 min. The mixture was then poured over cold 5% KHSO$_4$ then extracted using diethyl ether. Chromatography of the crude product over silica gel (93:7 toluene/ether) yielded 1.85 g (55%) pure (1R,3R,4S)-3-p-menthanyl 2-hydroxymethylbenzoate in the form of a colourless oil.

Analytical Data:

$^1$H-NMR(360 MHz, CDCl$_3$): 7.99 (dd, J=7.5, 1.2, 1H), 7.52 (ddd, J=7.5, 7.5, 1.6, 1H), 7.45 (dd, J=7.5, 1.2, 1H), 7.38 (ddd, J=7.5, 7.5, 1.6, 1H), 4.97 (ddd, J=11.0, 11.0, 4.3, 1H), 4.81 and 4.73 (AB of ABX, J=12.6, 7.1, 2H), 4.00 (t, J=7.1, 1H, exchanged with D$_2$O), 2.13 (m, 1H), 1.97 (m, 1H), 1.75 (m, 2H), 1.56 (m, 2H), 1.14 (m, 1H), 0.95 (d, J=6.7, 3H), 0.93 (d, J=7.1, 3H), 0.81 (d, J=7.1, 3H).

$^{13}$C-NMR(90.6 MHz, CDCl$_3$): 167.7 (s), 142.9 (s), 123.8 (d), 131.0 (d), 130.5 (d), 129.8 (s), 127.9 (d), 75.6 (d), 64.8 (t), 42.3 (d), 40.9 (t), 34.3 (t), 31.5 (d), 26.5 (d), 23.5 (t), 22.0 (q), 20.8 (q), 16.3 (q).

MS(CI, NH$_3$): 291 (1), 152 (100), 135 (52), 123 (5), 105 (10), 95 (2).

h) 3,7-Dimethyl-6-octenyl 2-hydroxymethylbenzoate 5 g (16.4 mmol) monocitronellyl (+)-phthalate was heated at reflux in 25 ml oxalyl chloride (18 eq.) for 3 h. The excess oxalyl chloride was distilled under vacuum. 5.3 g crude acid chloride was then diluted in 40 ml THF cooled to −8° under argon, and 1.87 g (3 eq.) NaBH$_4$ was added. The reaction mixture was maintained under stirring at 0° for 4 h, then at ambient temperature for 16 h. The reaction mixture was then cooled again to 0°, and then 10 ml methanol was added dropwise. After 15 min, the mixture was poured over cold 5% KHSO$_4$ then extracted using cold ethyl acetate. Chromatography of the crude product over silica gel (9:1 toluene/ether) yielded 1.41 g (31%) of almost pure 3,7-dimethyl-6-octenyl 2-hydroxymethylbenzoate in the form of a colourless oil.

Analytical Data:

$^1$HNMR(360 MHz, CDCl$_3$): 7.99 (dd, J=7.8, 1.2, 1H), 7.52 (ddd, J=7.5, 7.2, 1.2, 1H), 7.45 (dd, J=7.5, 1.2, 1H), 7.37 (ddd, J=7.8, 7.5, 1.2, 1H), 5.10 (m, 1H), 4.78 (d, J=7.2, 2H), 4.38 (m, 2H), 3.96 (t, J=7.2, 1H), 2.02 (m, 2H), 1.81 (m, 2H), 1.68 (s, 3H), 1.63 (m, 1H), 1.61 (s, 3H), 1.41 (m, 1H), 1.25 (m, 1H), 0.98 (d, J=6.5, 3H).

$^{13}$C-NMR(90.6 MHz, CDCl$_3$): 168.1 (s), 143.0 (s), 132.9 (d), 131.5 (s), 131.1 (d), 130.3 (d), 129.3 (s), 127.8 (d), 124.5 (d), 64.8 (t), 64.0 (t), 37.0 (t), 35.5 (t), 29.6 (d), 25.7 (q), 25.4 (t), 19.5 (q), 17.7 (q).

MS(CI, NH$_3$): 308 (1, M+NH$_4^+$), 291 (0.5, M+H$^+$), 174 (8), 169 (15), 152 (100), 135 (5), 105 (3).

i) 2-Phenylethyl 2-hydroxymethylbenzoate 25.2 g (93 mmol) monophenylethyl (−)-phthalate was heated at reflux in 50 ml oxalyl chloride (3 eq.) for 2 h. The excess oxalyl chloride was distilled under vacuum. The crude acid chloride was then diluted in 100 ml THF cooled to 0° under argon, and 7.4 g (2 eq.) NaBH$_4$ was added. The reaction mixture was maintained under stirring at ambient temperature for 1 h, then cooled to 0° and 20 ml of methanol was added. After leaving the reaction mixture under stirring at ambient temperature for 1 h it was poured over cold 5% KHSO$_4$ then extracted using diethyl ether. Chromatography of the crude product over silica gel (9:1 toluene/ether) yielded 12.1 g (47%) 2-phenylethyl 2-hydroxymethylbenzoate containing about 9% phthalide in the form of a white solid.

Analytical Data:

$^1$H-NMR(360 MHz, CDCl$_3$): 7.93 (dd, J=7.5, 1.1, 1H), 7.49 (ddd, J=7.5, 7.5, 1.1, 1H), 7.43 (dd, 3=7.5, 1.2, 1H), 7.36-7.24 (m, 6H), 5.10 (m, 1H), 4.73 (d, J=7.3, 2H), 4.54 (t, J=6.8, 2H), 3.84 (t, J=7.3, 1H), 3.08 (d, J=6.8, 2H).

$^{13}$C-NMR(90.6 MHz, CDCl$_3$): 167.9 (s), 143.0 (s), 137.6 (s), 133.0 (d), 131.1 (d), 130.2 (d), 129.0 (s), 128.9 (d), 128.6 (d), 127.8 (d), 126.7 (d), 65.9 (t), 64.6 (t), 35.1 (t).

j) (Z)-3-Hexenyl 2-hydroxymethylbenzoate 1 g (4.03 mmol) monohexenyl phthalate was heated at reflux in 6 ml oxalyl chloride (17.3 eq.) for 1.5 h. The excess oxalyl chloride was distilled under vacuum. The crude acid chloride was then diluted in 10 ml dichloromethane cooled to 0° under argon, and introduced dropwise on a solution of 2.07 g (2 eq.) nBuNBH$_4$ in 10 ml dichloromethane. The reaction mixture was maintained under stirring at O for 2.5 h. The mixture was then poured over 5% KHSO$_4$ and cold ethyl ethyl acetate, and extracted. Chromatography of the crude product over silica gel (85:15 cyclohexane/AcOEt) yielded 0.3 g (32%) (Z)-3-hexenyl 2-hydroxymethylbenzoate containing about 10% phthalide, in the form of a colourless oil.
Analytical Data:
$^1$H-NMR(360 MHz, CDCl$_3$): 8.00 (dd, J=7.6, 1.1, 1H), 7.52 (ddd, J=7.5, 7.5, 1.2, 1H), 7.45 (dd, J=7.5, 1.2, 1H), 7.37 (ddd, 3=7.6, 7.5, 1.2, 1H), 5.55 (m, 1H), 5.41 (m, 1H), 4.77 (broad s, 2H), 4.34 (t, J=6.9 Hz), 3.89 (broad signal, 1H), 2.54 (dd, J=13.9, 6.9, 2H), 2.10 (dq, J=13.9, 7.5, 2H), 0.97 (t, J=7.5, 3H).
$^{13}$C-NMR(90.6 MHz, CDCl$_3$): 168.0 (s), 143.0 (s), 134.9 (d), 133.0 (d), 131.1 (d), 130.3 (d), 129.1 (s), 127.8 (d), 123.6 (d), 65.0 (t), 64.8 (t), 26.8 (t), 20.7 (t), 14.2 (q).
MS(CI, NH$_3$): 252 (2, M+NH$_4^+$), 235 (10, M+H$^+$), 213 (5), 152 (100), 135 (10), 119 (2),105 (5), 94 (1).

k) (E)-3,7-Dimethyl-2,6-octadienyl 2-hydroxymethylbenzoate

A solution of 10.0 g geraniol (64.9 mmol). 9.6 g phthalic anhydride (1 eq.). 3.5 g diisopropyl-ethylamine (DIEA) (1 eq.) and 0.79 g 4-dimethylaminopyridine (0.1 eq.), in 130 ml dichloro-methane was maintained under stirring at ambient temperature for 24 h. The dichloromethane was concentrated then taken up in ethyl acetate, washed with 5% KHSO$_4$, then with water, dried over Na$_2$SO$_4$ and finally evaporated to obtain 19.0 g of a colourless oil. 5 g of the monophthalate thus obtained (16.6 mmol) was dissolved in 50 ml dichloromethane. 2.35 g DIEA (1.1 eq.) was added, then, at 5°, 2.26 g isobutyl chloroformiate (1 eq.) was added dropwise. The mixture was maintained under stirring at ambient temperature for 3 h, then 200 ml dichloromethane was added. The organic phase was then washed with water and dried over Na$_2$SO$_4$. The solvent was evaporated to obtain 6.34 g of slightly yellow oil. 1 g of this product (2.49 mmol) was then added dropwise to a solution at −20° of 0.38 g sodium borohydride (4 eq.) in 10 ml ethanol. After reacting for 30 min, the reaction medium was poured over a cold mixture of ethyl acetate and 5% KHSO$_4$. The organic phase was washed with water, dried over Na$_2$SO$_4$ then evaporated. The product was purified by chromatography over silica (8:2 cyclohexane/AcOEt). 0.36 g of a colourless oil was obtained with a yield of 50%.

$^1$H-NMR(360 MHz, CDCl$_3$): 8.01 (dd, J=7.5, 1.1, 1H), 7.51 (ddd, J=7.5, 7.5, 1.1, 1H), 7.44 (dd, J=7.5, 1.1), 7.37 (ddd, J=7.5, 7.5, 1.1, 1H), 5.51-5.44 (m, 1H), 5.13-5.06 (m, 1H), 4.86 (d, J=7.0, 2H), 4.77 (d, J=6.6, 2H), 3.93 (t, J=7.0, 1H), 2.18-2.04 (m, 4H), 1.78 (s, 3H), 1.68 (s, 3H), 1.61 (s, 3H).
$^{13}$C-NMR(90.6 MHz, CDCl$_3$): 168.1 (s), 143.1 (s), 142.9 (s), 132.9 (d), 131.9 (s), 131.2 (d), 130.4 (d), 129.3 (s), 127.8 (d), 123.7 (d), 117.9 (d), 64.8 (t), 62.3 (t), 39.6 (t), 26.3 (t), 25.7 (q), 17.7 (q), 16.6 (q).
MS(CI, NH$_3$): 306 (M+NH$_4^+$, 3),289 (M+H$^+$, 1), 107 (100),152 (35),137 (45).

l) 1-p-Menthen-8-yl 2-hydroxymethylbenzoate

A solution of 14.8 g phthalic anhydride (100 mmol), 15.4 g a-terpineol (100 mmol) and 1.22 g 4-dimethylamino-pyridine (10 mmol) was brought at reflux in 70 ml pyridine, over 16 h. 20 ml water was then added and brought at reflux for a further 20 min. The water and the pyridine were evaporated then taken up in ethyl acetate. Washing was performed with 5% KHSO$_4$ then with brine, drying over Na$_2$SO$_4$ then the solvent was evaporated to collect 16.9 g of a light brown oil. The residual pyridine and α-terpineol were eliminated by distillation in a bulb-to-bulb distillation apparatus before purifying over silica gel (9:1 cyclohexane/ethyl acetate and 1% AcOH) to obtain 9.1 g of a light brown oil. 3 g of the α-terpenyl monophthalate thus obtained (9.9 mmol) was dissolved in 30 ml dichloromethane and 1.4 g DIEA was added. The mixture was cooled to 0°, then 1.35 g isobutyl chloroformiate (9.9 mmol) was added dropwise and allowed to react at 0° for 1 h then at ambient temperature for 3 h. After addition of 75 ml dichloromethane, the mixture was washed 3 times with water then dried over sodium sulphate. The filtered dichloromethane solution was used for the latter stage. 0.6 g sodium borohydride (1.6 eq.) then 3 ml methanol was added dropwise. After 18 h at ambient temperature the reaction medium was poured over a cold mixture of ethyl acetate and 5% KHSO$_4$ under vigorous stirring. The organic solution was washed with brine, then dried over Na$_2$SO$_4$. The crude product was purified by chromatography over silica (90/10 cyclohexane/ethyl acetate). 1.65 g of very light brown oil was obtained with a yield of 17% in the 3 stages.
Analytical Data:
$^1$H-NMR(360 MHz, CDCl$_3$): 7.91 (dd, J=7.5, 1.2, 1 H), 7.49 (ddd, J=7.8, 7.5, 1.2, 1H), 7.41 (dd, J=7.5, 1.2, 1 H), 7.36 (ddd, J=7.8, 7.5, 1.2, 1H), 5.40 (broad s, 1H), 4.73 (d, J=7.3, 2H), 4.08 (t, J=7.3, 1H), 2.23 (m, 1H), 2.15-1.81 (m, 5H), 1.67 (s, 3H), 1.61 (s, 3H), 1.58 (s, 3H), 1.41 (m, 1H).
$^{13}$C-NMR(90.6 MHz, CDCl$_3$): 167.5 (s), 142.7 (s), 134.1 (s), 132.5 (d), 131.1 (s), 131.0 (d), 130.5 (d), 127.8 (d), 120.2 (d), 86.9 (s), 65.0 (t), 43.0 (d), 30.9 (t), 26.5 (t), 24.1 (t), 23.5 (q), 23.3 (q).
MS(CI, NH$_3$): 289 (M+H$^+$, 5), 170 (100), 152 (20), 137 (10).

m)(1'RE)-1,2,2-Trimethyl-4-(2',-2',-3'-trimethyl-3'-cyclopenten-1'-yl)-3-butenyl 2-hydroxymethylbenzoate 1.7 ml diisopropylethylamine (10 mmol) and 61 mg 4-dimethylaminopyridine (0.5 mmol) were added to a solution of 2.22 g polysantol (10 mmol) and 1.48 g phthalic anhydride (10 mmol) in 20 ml dichloromethane. The mixture was maintained under stirring for 72 h, then after adding ethyl acetate it was washed with 5% KHSO$_4$ and with brine. After drying over Na$_2$SO$_4$ and evaporating the solvents a brown oil was collected, used as for the following stage. 0.3 ml ethyl chloroformiate (3.1 mmol) was added at −10° to a solution of 1 g crude monophthalate (2.7 mmol) and 1.4 ml triethylamine (10 mmol) in methyl-tert-butyl ether (MTBE) (50 ml), and the mixture was maintained at this same temperature for 1 h under stirring. The mixture was then filtered over Celite and rinsed with 50 ml MTBE. The recovered filtrate was cooled to −10° and 420 mg NaBH$_4$ (10.8 mmol) was added. Ethanol was then added dropwise over a period of 30 min. After leaving to react for 1 h the reaction mixture was poured rapidly over a mixture of ethyl acetate and 5% KHSO$_4$ in water, the whole at 0° under vigorous stirring. The organic phase was dried over Na$_2$SO$_4$ then evaporated to collect a yellow oil which was chromatographed over silica gel (90/10 cyclohexane/ethyl acetate) to obtain 0.44 g (46%) of slightly yellow oil.
Analytical Data:
$^1$H-NMR(360 MHz, CDCl$_3$): 8.01 (~d, J=7.7, 1H), 7.58 (~d, J=7.5, 1H), 7.45 (~d, J=7.5, 1H), 7.38 (dd, J=7.7, 1H), 5.52 (m, 2H), 5.23 (m, 1H), 5.03 (q, J=6.3, 1H), 4.78 (m, 2H), 4.04 and 4.02 (2t, J=7.3, 1H), 2.37 (m, 1H), 2.23 (m, 1H), 2.08 (m, 1H), 1.60 (broad signal, 3H), 1.28 (d, 1=6.3 Hz, 3H), 1.12 (broad s, 6H), 0.94 and 0.91 (2s, 3H), 0.74 and 0.71 (2s, 3H).

$^{13}$C-NMR(90.6 MHz, CDCl$_3$): 167.5 (2s superimposed), 148.1 (2s), 143.1 (2s), 136.2 (2d), 132.9 (d), 131.0 (d), 130.4 (d), 129.9 (d), 129.7 (2s), 127.8 (d), 121.5 (d), 78.3 and 78.2 (2d), 64.9 (t), 54.4 (d), 48.1 (2s), 40.0 (s), 35.6 (s), 25.4 and 25.3 (2q), 24.1 (q), 23.7 (q), 23.4 (q), 20.5 and 20.4 (2q), 15.4 and 15.3 (2q), 12.7 (q).

MS(CI, NH$_3$): 374 (4, M+NH$_4^+$), 357 (2, M+H$^+$), 222 (10), 205 (100), 170 (40), 152 (10).

n) (E)-3,7-Dimethyl-2,6-octadienyl Dihydrocoumarate

Some ortho-coumaric acid was acetylated under conventional conditions to obtain ortho-acetyl coumaric acid with a yield of 49% after recrystallisation. 5.54 g (26.9 mmol) o-acetyl coumaric acid was then hydrogenated for 4 h in 50 ml methanol using 0.5 g 10% Pd-C to give 5.45 g (97%) o-acetyl dihydrocoumaric acid in the form of a white solid.

A mixture of 0.8 g (3.85 mmol) of this acid, 0.6 g (1 eq.) geraniol, 0.87 g (1.1 eq.) dicyclohexylcarbodiimide and 47 mg (0.1 eq.) 4-dimethylaminopyridine was maintained under stirring in 10 ml dichloromethane for 24 h. The reaction mixture was filtered, then diluted with ethyl acetate and washed successively with 5% KHSO$_4$, 5% NaHCO$_3$, and with brine. Following chromatography over silica gel (95:5 cyclohexane/ethyl acetate) 0.62 g (58%) geranyl o-acetyl dihydrocoumarate was obtained.

The acetyl was deprotected at −15° in a mixture of 4 eq. MeONa in methanol (30 ml/mmol) in 3 h. Diethyl ether was added, washing was performed with 5% KHSO$_4$, drying with 5% Na$_2$SO$_4$, and the solvent was evaporated. The yield was 27%.

Analytical Data:

$^1$H-NMR(360 MHz, CDCl$_3$): 7.10 (m, 2H), 6.86 (m, 2H), 5.29 (tq, J=7.4, 1.2, 1H), 5.07 (tq, J=6.6, 1.2, 1H), 4.60 (d, J=7.4, 1H), 2.90 (t, J=6.5, 2H), 2.71 (t, J=6.5, 2 H), 2.06 (m, 4H), 1.67 (broad s, 6H), 1.59 (broad s, 3H).

$^{13}$C-NMR(90.6 MHz, CDCl$_3$): 175.7 (s), 154.4 (s), 142.9 (s), 131.9 (s), 130.6 (d), 128.0 (d), 127.4 (s), 123.7 (d), 120.8 (d), 117.8 (d), 117.3 (d), 62.2 (t), 39.5 (t), 35.3 (t), 29.7 (t), 26.3 (t), 25.7 (q), 24.7 (t), 22.7 (t), 17.7 (q), 16.5 (q).

o) (Z)-3-Hexenyl dihydrocoumarate 2.08 g (10 mmol) o-acetyldihydrocoumaric acid, 1.0 g (10 mmol) (Z)-3-hexenol, 2.06 g (1 eq.) dicyclohexylcarbodiimide and 70 g (0.057 eq.) 4-dimethyl-aminopyridine were stirred into 40 ml dichloromethane for 16 h. The mixture was subsequently filtered then diluted using ethyl acetate, then washed successively with 5% KHSO$_4$, 5% NaHCO$_3$, and with brine. Chromatography of the product over silica gel (9:1 cyclohexane/ethyl acetate) yielded 1.78 g (61%) (Z)-3-hexenyl o-acetyl dihydrocoumarate. 100 mg (0.34 mmol) of this product was then deacetylated by reacting with 100 μl 5.4 M MeONa in 10 ml methanol for 1 h at −10°. Following conventional treatment, 80 mg (94%) (Z)3-hexenyl dihydrocoumarate was obtained in the form of a colourless oil.

Analytical Data:

$^1$H-NMR(360 MHz, CDCl$_3$): 7.08 (m 2H), 6.86 (m, 2H), 5.47 (m, 1H), 5.26 (m, 1H), 5.41 (m, 1H), 4.08 (t, 3=7.1, 2H), 2.90 (m, 2H), 2.70 (m, 2H), 2.34 (dt, J=13.8, 7.1, 2H), 2.01 (dq, J=15.0, 7.6, 2H), 0.94 (t, J=7.6, 3H).

$^{13}$C-NMR(90.6 MHz, CDCl$_3$): 175.6 (s), 154.3 (s), 134.8 (d), 130.5 (d), 128.0 (d), 127.3 (s), 123.4 (d), 120.8 (d), 117.1 (d), 64.8 (t), 35.1 (t), 26.6 (t), 24.7 (t), 20.6 (t), 14.2 (q).

MS(ESI): 248.9 (100, M+H$^+$, 167.2 (75).

p) (Z)-3-Hexenyl 3-endo-hydroxymethyl-bicyclo[2.2.1] hept-5-ene-2-endo-carboxylate A mixture of 2 g (20 mmol) (Z)-3-hexenol, 3.28 g (20 mmol) bicyclo[2.2.1]hept-5-ene-anhydride-2,3-endo-dicarboxylic, 3.5 ml (20 mmol) diisopropylethylamine and 61 mg (0.5 mmol) 4-dimethylaminopyridine in 40 ml dichloromethane was maintained under stirring at ambient temperature for 24 h. This was then diluted in ethyl acetate and washed using with 5% KHSO$_4$ and brine. 5.1 g (97%) of a pale yellow solid, i.e. (Z)3-hexenyl 3-endo-carboxy-bicyclo[2.2.1]hept-5-ene-2-endo-carboxylate, was obtained.

A mixture of 5.1 g (19.3 mmol) of this monoacid and 3.5 ml (40 mmol) oxalyl chloride was maintained under stirring for 2 h at ambient temperature. The excess oxalyl chloride was then evaporated and 40 ml dichloromethane was added. After adding 6.2 g (1.2 eq.) tetrabutylammonium borohydride, the reaction mixture was maintained under stirring for 2 h. The mixture was then poured into cold 5% KHSO$_4$ and after extraction of the product from cold ethyl acetate, 4.8 g (99%) of a pale yellow oil was obtained. Rapid filtration over silica gel (60:40 cyclohexane/ethyl acetate) yielded 1.6 g (32%) (Z)-3-hexenyl 3-endo-hydroxymethyl-bicyclo[2.2.1]hept-5-ene-2-endo-carboxylate in the form of a pale yellow oil.

Analytical Data:

$^1$H-NMR(360 MHz, CDCl$_3$): 6.22 (dd, J=5.6, 2.5, 1H), 6.10 (dd, 7=5.6, 2.7, 1H), 5.52 (m, 1H), 5.31 (m, 1H), 4.05 (m, 2H), 3.49 (dd, J=11.6, 5.7, 1H), 3.42 (dd, J=11.6, 8.7, 1H), 3.16 (s, 1H), 3.14 (m, 1H), 2.90 (broad signal, 1H), 2.69 (m, 1H), 2.38 (m, 2H), 2.07 (m, 2H). 1.39 (m, 2H), 0.98 (t, J=7.6, 3H).

$^{13}$C-NMR(90.6 MHz, CDCl$_3$): 174.6 (s), 136.0 (d), 134.7 (2d superimposed), 123.8 (d), 64.2 (t), 64.0 (t), 48.8 (t), 47.33 and 47.30 (2d), 46.4 (d), 45.9 (d), 26.7 (t), 20.7 (t), 14.2 (q).

MS(CI, NH$_3$): 268 (35, M+NH$_4^+$), 251 (100, M+H$^+$), 186 (5), 168 (40), 151 (5), 136 (5),119 (2), 106 (2).

EXAMPLE 2

Tests in a Basic Medium

A number of tests were conducted at different pH values on compounds of the invention to test the hydrolysis of the ester function in accordance with the following general methods.

General Methods a) At t=0, 10 ml of a 0.001 M solution of compound of the invention in dioxane was added rapidly to 40 ml of a buffer solution (7:1 water/dioxane) at pH 7, containing Cremophor RH-40 (BASF) to prevent emulsion. The buffer solution was prepared by dissolving two tablets of borate buffer (Fluka) in a mixture of 175 ml water and 25 ml dioxane. Hydrolysis was followed at ambient temperature until the reaction was complete by photometry by recording the optical absorption of the solution within a wavelength range of 260 to 360 nm at discrete time intervals and at a scanning rate of 960 nm/min.

b) Buffer solutions at pH 7 and 9.2 respectively were prepared by dissolving two tablets of borate or phosphate buffer (Fluka) in a mixture of 175 ml water and 25 ml dioxane or acetonitrile. 70 to 100 mg of compound of the invention was dissolved in 50 ml dioxane or acetonitrile and 0.3 ml of this solution was added to 1.2 ml of the buffer solution (pH 7 or 9.2). The mixture was immediately injected in a HPLC (high-pressure liquid chromatography) apparatus (at t=0) and eluted at 1 ml/min with a water/acetonitrile gradient varying between 70:30 and 20:80 (for 20 min) over an inverse-phase column (Macherey-Nagel Nucleosil 100-5 C 18, 250×4 mm). The sample, which was temperature-regulated to 20°, was re-injected every 30 min or every hour.

Using at least one of the two methods cited (HPLC or photometry), hydrolysis of the following compounds with release of a fragrant alcohol, under the above-mentioned pH conditions, was thus verified: 3,7-dimethyl-6-octenyl 2-formylbenzoate, (E)-3,7-dimethyl-2,6octadienyl 2-formylbenzoate, (Z)-3,7-dimethyl-2,6-octadienyl 2-formylbenzoate, 2-phenylethyl 2-formylbenzoate, (E)-3,7-dimethyl-2,6octadienyl 2-acetylbenzoate, 3,7-dimethyl-4-octenyl 2-acetylbenzoate, (1R,3R,4S)-3-p-menthanyl 2-acetylbenzoate, (1R,3R,4S)-3-p-menthanyl 2-hydroxymethylbenzoate, 3,7-dimethyl-6-octenyl 2-hydroxymethylbenzoate, 2-phenylethyl 2-hydroxymethyl-benzoate, (Z)-3-hexenyl 2-hydroxymethyl-benzoate, (E)-3,7-dimethyl-2,6-octadienyl 2-hydroxymethylbenzoate, 1-p-menthen-8-yl 2-hydroxymethylbenzoate, (1'R,E)-1,2,2-trimethyl-4-(2',2',3'-trimethyl-3'-cyclopenten-1'-yl)-3-butenyl 2-hydroxymethyl-benzoate, (Z)3-hexenyl dihydrocoumarate, (E)-3,7-dimethyl-2,6-octa-dienyl dihydrocoumarate, and (Z)3-hexenyl 3-endo-hydroxymethyl-bicyclo[2.2.1]hept-5-ene-2-endo-carboxylate.

EXAMPLE 3

Test on Textiles

A number of tests were conducted on compounds -of the invention to test the hydrolysis of the latter following a washing cycle on a device of the Linitest® type. 0.144 ml of a solution (10% in ethanol) of a compound of the invention or respectively 0.072 ml of a solution (10% in ethanol) of the corresponding free alcohol (roughly corresponding to the equivalent molar quantity) were added to 1.8 g of an unperfumed textile softener containing Esterquats (Stepantex® and Stepanquat®) of the following composition:

| Ingredients | % by weight |
| --- | --- |
| Stepantex ® VS90 or VHR 90* | 16.7 |
| Stepanquat ® F* | 0.4 |
| 1% colorant solution** | 0.3 |
| Water | 82.6 |
| Total | 100.0 |

*Source: Stepan, France
**Sandolan Milling Blue N-LN180; source: Clariant, Switzerland Linitest® Washing Method A standard cotton towel (28×28 cm) is placed in a Linitest® 600-ml stainless steel container. 1.8 g standard non-perfumed detergent base (for example Henkel, ECE Colour Fastness Test Detergent 77) and 400 ml cold tap water are added. The closed containers are placed in the Linitest® machine (Heraeus) and then left in a bath at 44° for 20 min under stirring. The towels are then removed and rinsed twice in a beaker, each time with 600 ml cold tap water. Rinsing with the softener is then performed in a beaker containing 600 ml cold water with 1.8 g of the softener containing in one case one of the precursor compounds of the invention (test A), and in the other case the corresponding free alcohol (test B). The towel is agitated for 5 min then wrung out by hand. Weighing is performed to ensure the same quantity of residual water in all the cloths so as not to bias the comparison between precursors and free alcohols.

Each test was performed twice. A total of 11 panellists compared, in a blinding test, the different towels still wet after washing, then dry after 1 and 6 days respectively. To avoid contamination, the dry towels were kept in large, closed crystallising dishes between evaluations. Each panellist indicated the intensity of the odour of each sample on a scale of 1 (no odour) to 10 (very strong odour), and the sample preferred between test A (precursor) and test B (free alcohol).

According to the procedure described above, 3,7-dimethyl-6-octenyl 2-formylbenzoate (I) (test A) was compared with citronellol (test B), (E)-3,7 diethyl-2,6-octadienyl 2-formylbenzoate (II) (test A) was compared with geraniol (test B), a mixture of (E and Z)-3,7-dimethyl-2,6-octadienyl 2-formylbenzoate (II) (test A) was compared with a mixture of geraniol and nerol (test B), 2-phenylethyl 2-formylbenzoate (IV) (test A) was compared with 2-phenylethanol (test B), (E)-3,7-dimethyl-2,6-octadienyl 2-acetylbenzoate (V) (test A) was compared with geraniol (test B), and 3,7-dimethyl-6-octenyl 2-acetylbenzoate (VI) (test A) was compared with citronellol (test B). The following table summarizes the results of the panel: each panellist compared a precursor according to the invention to the corresponding free alcohol, indicating on the one hand the odor intensity of each test on a scale of 1 to 10; the table gives the calculated average intensity for each sample; and on the other hand the preference of the panellist for test A or test B, the number in brackets corresponding to the number of panellists preferring the respective sample.

| Product | Wet towel | Dry towel (1 day) | Dry towel (6 days) |
| --- | --- | --- | --- |
| 3,7-Dimethyl-6-octenyl 2-formylbenzoate (I) | 6.1 (3) | 3.8 (10) | 5.3 (10) |
| Citronellol | 6.4 (8) | 2.5 (1) | 2.9 (1) |
| 3,7-Dimethyl-2,6-octadienyl 2-formylbenzoate (II) | 7.4 (9) | 6.1 (10) | 4.3 (9) |
| Geraniol | 5.0 (2) | 3.4 (1) | 2.3 (2) |
| (E and Z)-3,7-Dimethyl-2,6-octadienyl 2-formylbenzoate (III) | 4.9 (8) | 3.8 (9) | 5.5 (10) |
| Geraniol/Nerol | 5.3 (3) | 3.3 (2) | 2.9 (1) |
| 2-Phenylethyl 2-formyl-benzoate (IV) | 5.4 (5) | 4.7 (9) | 5.2 (10) |
| Phenylethanol | 5.1 (6) | 3.9 (2) | 2.6 (1) |
| (E)-3,7-Dimethyl-2,6-octadienyl 2-acetylbenzoate (V) | 5.0 (7) | 2.8 (5) | 4.5 (11) |
| Geraniol | 4.5 (4) | 2.6 (4) | 3.3 (0) |
| 3,7-Dimethyl-6-octenyl 2-acetylbenzoate (VI) | 3.5 (3) | 2.5 (7) | 3.9 (7) |
| Citronellol | 7.4 (8) | 2.3 (4) | 2.7 (4) |

It was thus observed that, in the majority of cases, the average intensity determined by the panellists diminished when going from the wet towels to the dry ones (1 day). Two different behaviours are then observed, for the free alcohol and the precursor, by comparing the intensity evaluated after 1 and 6 days on the dry linen. Whereas generally the intensity of the free alcohol diminishes, that of the precursor increases. Moreover although, on wet washing, the odour of the free alcohol has often been perceived as being more intense than that of the alcohol released from the compounds of the invention, on dry washing this effect is reversed, and the intensity of the alcohol released by the products of the invention (test A) was perceived as more intense than that of the free alcohol (test B). This effect very clearly reveals that the desired aim was achieved when using the compounds of the invention. Furthermore, the majority of the panellists preferred the dry sample originating from test A (precursor), after as little as 1 day. After 6 days this effect was even more pronounced, when a very large majority of the panellists (between 7 and 11 panellists out of 11) preferred the sample corresponding to the precursor.

EXAMPLE 4
Tests on Textiles

A number of tests were conducted on compounds of the invention to test the hydrolysis following a washing cycle in a washing machine.

Method of Washing in a Washing Machine

About 1 kg of standard towels measuring 28×28 cm were washed at 40° in a washing machine (Miele, Deluxe electronic model W724) without prewashing, using 50 g of a standard base detergent (for example Henkel, ECE Colour Fastness Test Detergent 77) and 50 g of a currently available unperfumed softener containing Esterquats.

The textile softening base was of the following composition:

| Ingredients | % by weight |
|---|---|
| Mixture of HEQ-Esterquat*/fatty acid $C_{16}$-$C_{18}$ (6:1) | 14.00 |
| Tallowyl ethoxylate from coconut 20EO | 0.75 |
| Tallowyl alcohol | 0.75 |
| Water | 84.50 |
| Total | 100.00 |

*2,3-di($C_{16}$–$C_{18}$-acyloxy)propyltriethylammonium chloride

In two separate tests, towels were treated in accordance with this general method using as the additive of the textile softener, respectively one of the compounds of the invention (0.8% by weight) in test A and free alcohol (0.3% by weight) in test B. The two groups of towels were subjected to a blind test evaluation on their removal from the washing machine and 24 h later.

Following this procedure, 3,7-dimethyl-6-octenyl 2-formylbenzoate (test A) was compared with citronellol (test B), (E)-3,7-dimethyl-2,6-octadienyl 2-acetylbenzoate (test A) was compared with geraniol (test B), 2-phenylethyl 2-hydroxymethylbenzoate (test A) was compared with 2-phenylethanol (test B), and (E)-3,7-dimethyl-2,6-octadienyl 2-hydroxymethylbenzoate (test A) was compared with geraniol (test B). Whereas, on wet fabrics, the towels treated in test B seemed more odoriferous than those treated in test A, 24 h after the wash the latter proved to develop a much more intense odour than those in test B, and the odour persisted for several days after the wash.

EXAMPLE 5
Test on Textiles

Two groups of standard terry towels were treated separately and in an identical way as described in Example 4, by adding 0.8% (E)-3,7-dimethyl-2,6-octadienyl 2-formylbenzoate in test A and 0.13% geraniol in test B to the softening base. The towels were evaluated under blind conditions by 40 panellists in a triangular test, 20 of whom had the cloths from test A as the sole sample, and 20 those from test B. On wet fabrics, 30 of the 40 panellists correctly distinguished between the samples. Furthermore, 20 of these 30 people preferred the geraniol (test B), and 26 judged it to be the stronger. After 24 h, the triangular test was repeated on dry towels. This time, 31 of the 40 panellists distinguished correctly between the samples, and 29 of the 31 preferred the (E)-3,7-dimethyl-2,6-octadienyl 2-formylbenzoate (test A). 27 found the test-A sample to be the more powerful.

EXAMPLE 6
Ironing Test on Textiles
General Method of Treating the Textiles

Washing tests were conducted on a total weight of washing of 1.5 kg, including 5 100%-cotton pillowcases (65×65 cm) and 4 100%-cotton towels (87 cm×43 cm). The fabrics were washed at 40° in a washing machine (Miele, Deluxe electronic model W724), without prewashing, using 50 g of a standard detergent base (for example Henkel, ECE Colour Fastness Test Detergent 77) and 50 g of unperfumed softener containing Ester Quats (Stepantex®).

The textile softener base used was of the following composition:

| Ingredients | % by weight |
|---|---|
| Stepantex ® VS90* | 16.5 |
| $CaCl_2$ (10% in solution) | 0.2 |
| Colorant 1% solution* | 0.3 |
| Water | 83.0 |
| Total | 100.0 |

*see Example 3

In the 4 independent tests, the pillow cases were washed following the method indicated above with the base containing 0.3% precursor substances according to the invention, that is to say, 2-phenylethyl 2-formylbenzoate (A), 3,7-dimethyl-6-octenyl 2-acetyl-benzoate (B), or (E)-3,7-dimethyl-2,6-octadienyl 2-acetylbenzoate (C). The pillow cases were left in the open air to dry. After 24 h, the cases were ironed using a Philips Excel Plus Steam iron, and the perfuming effect following the ironing operation was evaluated by a panel of experts on a blind test. It then emerged very clearly that the perfume corresponding to the fragrant alcohol present in each of the precursors was perceived in a significant manner when released by the action of heat and/or of the steam produced by the iron. Precursor A produced the most pronounced odoriferous effect, followed by C and then B.

What is claimed is:
1. A compound of formula

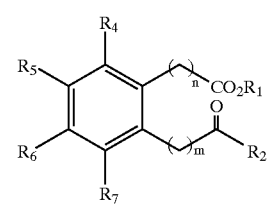

(I)

in which $R_1$ represents a radical belonging to a fragrant alcohol of the formula $R_1OH$, m and n define whole numbers within the range 0 to 1 such that the sum m+n is equal to 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted, and provided that menthyl 2-acetylbenzoate, benzyl 2-formylbenzoate, octyl 2-formylbenzoate, benzyl 2-acetylbenzoate and menthyl 2-formylbenzoate are excluded.

2. A compound according to claim 1, characterised in that it is capable of assuming a constrained conformation in which the distance between the oxygen of the hydroxy group and the carbon of the ester function does not exceed 2.8

Angstrom for a molecular energy calculated by the method MM2 which differs by no more than 3 kcal/mol from the minimum total energy of the molecule.

3. A compound according to claim 2, wherein $R_2$ defines a hydrogen or a methyl group.

4. A compound according to claim 2 wherein the residue of the said compound following release of the perfuming alcohol is odorless.

5. A compound of the formula

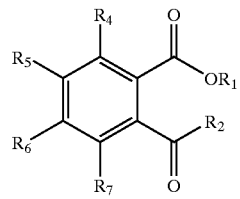

(Ia)

in which the symbols $R_1$, $R_2$ and $R_4$ to $R_7$ are defined as in claim 1.

6. A perfuming composition or perfumed article containing, as an active ingredient, a compound according to claim 5.

7. A perfumed article according to claim 6 in the form of an after-shave lotion, of a cosmetic preparation, of a soap, of a shampoo or conditioner or another hair-care product, of a bat or shower gel, or a foam bath, of a body deodorant or of an air freshener, of a detergent or textile softener, or of an all-purpose product.

8. A compound according to claim 1 wherein the residue of the said compound following release of the perfuming alcohol is odorless.

9. A perfuming composition or perfumed article containing, as an active ingredient, a compound according to claim 1.

10. A perfumed article according to claim 9 in the form of an after-shave lotion, of a cosmetic preparation, of a soap, of a shampoo or conditioner or another hair-care product, of a bath or shower gel, or a foam bath, of a body deodorant or of an air freshener, of a detergent or textile softener, or of an all-purpose product.

11. A perfuming composition or perfumed article according to claim 9, wherein the active compound of formula (I) is such that R2 defines a hydrogen or a methyl group.

12. A perfuming composition or perfumed article according to claim 9, wherein the compound of formula (I) is capable of assuming a constraint conformation in which the distance between the oxygen and the hydroxy group and the carbon of the esteric function does not exceed 2.8 Angstrom for a molecular energy calculated by the method MM2 which differs by no more than 3 kcal/mol for the minimum total energy of the molecule.

13. A compound selected from the group consisting of 3,7-dimethyl-6-octenyl 2-formylbenzoate, (E or Z)-3,7-dimethyl-2,6-octadienyl 2-formylbenzoate, 2-phenylethyl 2-formylbenzoate, (E)-3,7-dimethyl-2,6-octadienyl 2-acetylbenzoate and 3,7-dimethyl-6-octenyl 2-acetylbenzoate.

14. A perfuming composition or perfumed article containing, as an active ingredient, a compound according to claim 13.

15. A perfumed article according to claim 14 in the form of an after-shave lotion, of a cosmetic preparation, of a soap, of a shampoo or conditioner or another hair-care product, of a bath or shower gel, or a foam bath, of a body deodorant or of an air freshener, of a detergent or textile softener, or of an all-purpose product.

16. A process for perfuming textiles subjected to washing in the presence of a detergent followed optionally by a treatment with a textile softener, the process being characterised in that the said detergent and/or the said softener contains a compound of formula (I)

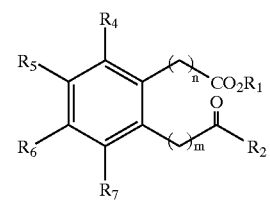

(I)

in which $R_1$ represents a radical belonging to a fragrant alcohol of the formula $R_1OH$, m and n define whole numbers within the range 0 to 1 such that the sum m'n is equal to 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted.

17. A process for prolonging the effect of diffusion of the characteristic odor of a fragrant alcohol developed by textiles, wherein the textiles are subjected to a washing cycle in the presence of a detergent and, optionally to a subsequent treatment with a textile softener, the said detergent and/or softener containing a compound of formula (I)

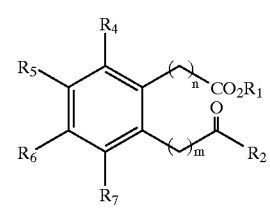

(I)

in which $R_1$ represents a radical belonging to a fragrant alcohol of the formula $R_1OH$, m and n define whole numbers within the range 0 to 1 such that the sum m+n is equal to 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted.

* * * * *

UNITED STATES PATENT AND TRADEMARK OFFICE
CERTIFICATE OF CORRECTION

PATENT NO. : 6,589,921 B2
DATED : July 8, 2003
INVENTOR(S) : Herrmann et al.

It is certified that error appears in the above-identified patent and that said Letters Patent is hereby corrected as shown below:

<u>Title page,</u>
Item [56], References Cited, OTHER PUBLICATIONS,
"N. Gautier and R.H. Dodd" reference, delete "Communicaitions" and insert
-- Communications --.

<u>Column 23,</u>
Line 1, delete "Angstrom" and insert -- Angström --;
Line 28, delete "bat" and insert -- bath --; and
Line 44, delete "R2" and insert -- $R_2$ --.

<u>Column 24,</u>
Line 28, delete "m'n" and insert -- m+n --.

Signed and Sealed this

Fourteenth Day of October, 2003

JAMES E. ROGAN
*Director of the United States Patent and Trademark Office*